(12) United States Patent
Laszlo et al.

(10) Patent No.: US 8,455,666 B1
(45) Date of Patent: Jun. 4, 2013

(54) VEGETABLE OIL ESTERIFIED LIPOIC ACID

(75) Inventors: Joseph A. Laszlo, Peoria, IL (US);
David L. Compton, Peoria, IL (US);
Kervin O. Evans, Chillicothe, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/224,565

(22) Filed: Sep. 2, 2011

(51) Int. Cl.
*C07D 339/04* (2006.01)
(52) U.S. Cl.
USPC .......................................................... 549/39
(58) Field of Classification Search
USPC ............................................................ 549/39
See application file for complete search history.

(56) References Cited

U.S. PATENT DOCUMENTS

| | | | |
|---|---|---|---|
| 5,670,657 A * | 9/1997 | Kojima et al. ............ | 549/39 |
| 6,346,236 B1 | 2/2002 | Compton et al. | |
| 7,163,673 B2 | 1/2007 | Compton et al. | |
| 7,572,610 B2 | 8/2009 | Laszlo et al. | |
| 7,727,514 B2 | 6/2010 | Laszlo et al. | |
| 7,744,856 B2 | 6/2010 | DeFillipi et al. | |
| 2010/0098653 A1 | 4/2010 | Yu et al. | |

FOREIGN PATENT DOCUMENTS

WO WO 2011/078785 * 6/2011

OTHER PUBLICATIONS

Nu-Check Prep catalog, obtained from <http://www.nu-chekprep.com/10_11_catalog.pdf>, accessed Oct. 11, 2012, p. 1-5, 11 and 13 provided.*
Wang et al, 2009, Journal of Food Lipids, vol. 16, p. 113-132.*
Koufaki, et al., "Multifunctional Lipoic Acid Conjugates" Current Medicinal Chemistry, 2009, vol. 16, pp. 4728-4742.

* cited by examiner

*Primary Examiner* — Wu-Cheng Winston Shen
*Assistant Examiner* — Karen Cheng
(74) *Attorney, Agent, or Firm* — John Fado; Randall E. Deck; Lesley Shaw (57) ABSTRACT

Esters of lipoic acid with a glyceride are produced in high yield by lipase catalyzed transesterification. The esters are generally characterized by Formula 1:

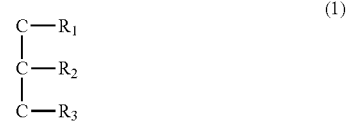

wherein at least one but no more than two of $R_1$, $R_2$, and $R_3$ are a lipoic acid derivative selected from a lipoate moiety of the formula:

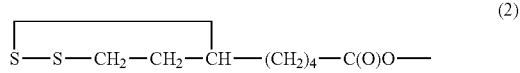

or a dihydrolipoate moiety of the formula

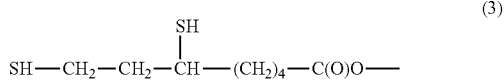

and the other of the $R_1$, $R_2$, and $R_3$ are independently selected from $C_4$ to $C_{24}$ fatty acid moieties or OH, with the proviso that at least one of the $R_1$, $R_2$, and $R_3$ is a fatty acid moiety.

10 Claims, 6 Drawing Sheets

VEGETABLE OIL ESTERIFIED LIPOIC ACID

BACKGROUND OF THE INVENTION

1. Field of the Invention

This invention relates to lipoic acid esters of vegetable oils, their method of preparation, and their use.

2. Description of the Prior Art

Reactive oxygen, nitrogen, and sulfur species (collectively, reactive species) are understood to be likely causative agents in inflammatory and aging processes. Enzymatic and non-enzymatic antioxidants counter reactive specie generation and propagation to help preserve extra- and intracellular structures (e.g., membranes) and macromolecules (e.g., DNA, proteins) (Lü et al., Chemical and molecular mechanisms of antioxidants: Experimental approaches and model systems. *J. Cell. Mol. Med.* 2010, 14:840-860). Antioxidant hydro/lipophilicity dictates the extent to which an antioxidant compartmentalizes, and therefore determines which molecules are afforded protection. A variety of natural antioxidants are lipophilic (e.g., tocopherols, carotenoids) and aqueous-soluble ones can be made so (Shahidi and Zhong, Novel antioxidants in food quality preservation and health promotion. *Eur. J. Lipid Sci. Technol.* 2010, 112:930-940). Plant-derived phenolics are highly regarded for their antioxidant capacity. Hydroxycinnamates are a class of phenolics that are readily converted to lipophilic molecules. We recently demonstrated that a triglyceride comprised of ferulic acid and two oleic acid groups stably incorporates into model lipid membranes and provides antioxidant capacity to the membrane (Laszlo et al., Feruloyl dioleoylglycerol antioxidant capacity in phospholipid vesicles. *J. Agric. Food. Chem.* 2010, 58:5842-5850). To gain further insight into the effectiveness of glyceride-based antioxidants in preserving membrane components from oxidative events, a variety of lipophilic antioxidants need to be examined.

α-Lipoic acid (ALA) and dihydrolipoic acid (DHLA) are natural antioxidants in humans, and as such are the subject of intense investigation. The metabolic functions and uses of lipoic acid in disease prevention have been recently reviewed (Ghibu et al., Antioxidant properties of an endogenous thiol: Alpha-lipoic acid, useful in the prevention of cardiovascular diseases. *J. Cardiovasc. Pharmacol.* 2009, 54:391-398). Biewenga and colleagues summarized the pharmacology of ALA and its role in mitigating oxidative stress (Biewenga et al., The pharmacology of the antioxidant: Lipoic acid. *Gen. Pharmacol.* 1997, 29:315-331). Mitochondrial components are particularly sensitive to free radical damage, which can lead to lower mitochondrial performance and programmed cell death. Lipoic acid acts to prevent such damage (Palaniappan, A. R.; Dai, A., Mitochondrial ageing and the beneficial role of α-lipoic acid. *Neurochem. Res.* 2007, 32:1552-1558). Many patented ALA derivatives have been prepared, including polymeric forms (Packer et al., Lipoic acid analogs. U.S. Pat. No. 6,387,945, 2002; and Yu and Lee, Antioxidant polymers containing [1,2]-dithiolane moieties and uses thereof. U.S. 2010/009865 A1 2010). Koufaki and colleagues provide a comprehensive review of ALA conjugates (esters and amides) for therapeutic interventions, demonstrating the synergetic potential of covalently linked multifunctional molecules (Koufaki et al., Multifunctional lipoic acid conjugates. *Curr. Med. Chem.* 2009, 16:4728-4742). Many of ALA's capabilities are linked to its antioxidant capacity (Packer and Cadenas, Lipoic acid: Energy metabolism and redox regulation of transcription and cell signaling. *J. Clin. Biochem. Nutr.* 2011, 48:26-32). A mixture of lipoic acid and hydroxycinnamic acids was shown to be a potent antioxidant combination, with the hydroxycinnamate serving to reduce oxidized lipoic acid (Lu and Liu, Interactions of lipoic acid radical cations with vitamins c and e analogue and hydroxycinnamic acid derivatives. *Arch. Biochem. Biophys.* 2002, 406:78-84). Lee and colleagues prepared lipoic acid esters of polyols, including glycerol, and prepared antioxidant nanospheres (200-600 nm) from them for therapeutic uses (Lee et al., Preparation and characterization of antioxidant nanospheres from multiple α-lipoic acid-containing compounds. *Bioorg. Med. Chem. Lett.* 2009, 19:1678-1681). HOCl (hypochlorous acid) led to rapid consumption of the nanospheres. These spheres were shown to protect 1-antiproteinase from oxidation by HOCl (produced by halogenation of hydrogen peroxide by myeloperoxidase). HOCl can in turn generate highly reactive hydroxyl radical species that may attack polyunsaturated lipids. It was demonstrated that DHLA, but not ALA, was effective in preventing peroxidation of linoleic acid or human non-HDL fraction catalyzed by lipoxygenases (Lapenna et al., Dihydrolipoic acid inhibits 15-lipoxygenase-dependent lipid peroxidation. *Free Radical Biol. Med.* 2003, 35:1203-1209). DHLA was an effective scavenger of stable free radicals such as DPPH in ethanol. The mode of action for DHLA was ascribed to its ability to inactivate lipoxygenase, and possibly from scavenging fatty acid peroxyl radicals generated by the enzyme. Thus, ALA scavenges hydroxyl radicals, HOCl and singlet oxygen, while DHLA additionally provides protection against weaker oxidants. ALA and DHLA demonstrate beneficial health effects for a multiplicity of tissues and organs.

As with other major organs, skin tissues are subject to a broad array of environmental assaults (e.g., UV light, ozone), diseases, and age-related changes that result in inflammation, cosmetic alterations, and aging (Yamasaki and Gallo, The molecular pathology of rosacea. *J. Dermatol. Sci.* 2009, 55:77-81). It was reported that DHLA significantly inhibited the priming and activation stages of skin inflammation induced by topical 12-O-tetradecanoylphorbol-13-acetate application to mouse skin (Ho et al., Dihydrolipoic acid inhibits skin tumor promotion through anti-inflammation and anti-oxidation. *Biochem. Pharmacol.* 2007, 73:1786-1795). Tsuji-Naito and coworkers demonstrated that the zinc complex of an aqueous-soluble dihydrolipoic acid derivative was effective in suppressing melanin formation in skin melanocytes by combining with tyrosinase reaction products (Tsuji-Naito et al., Modulating effects of a novel skin-lightening agent, α-lipoic acid derivative, on melanin production by the formation of dopa conjugate products. *Bioorg. Med. Chem.* 2007, 15:1967-1975). Mouse fibroblasts exposed to ALA had lower expressed matrix metalloproteinase-2 activity, indicating a positive dermal influence would be expected with the antioxidant (Voronkina et al., Activity of matrix metalloproteinases in normal and transformed mouse fibroblasts exposed to antioxidants. *Cell Tissue Biol.* 2009, 3:56-60). Topical treatments with antioxidants such as ALA derivatives are anticipated to have an anti-aging influence on skin (Han and Nimni, Transdermal delivery of amino acids and antioxidants enhance collagen synthesis: In vivo and in vitro studies. *Connect. Tissue Res.* 2005, 46:251-257; and Herschthal and Kaufman, Cutaneous aging: A review of the process and topical therapies. *Expert Rev. Dermatol.* 2007, 2:753-761).

Topical delivery of active agents may avoid the metabolic modification issues associated with oral administration and non-target organ influences (Bhatti et al., Mechanisms of antioxidant and pro-oxidant effects of α-lipoic acid in the diabetic and nondiabetic kidney. *Kidney Int.* 2005, 67:1371-1380; and Hsieh et al., Quercetin and ferulic acid aggravate renal carcinoma in long-term diabetic victims. *J. Agric. Food.*

Chem. 2010, 58:9273-9280). Liposomal vesicles can serve as cutaneous delivery vehicles for antioxidants or as stabilized carriers of oxidation sensitive cosmeceuticals (medicinal cosmetics) and drugs (El Maghraby et al., Liposomes and skin: From drug delivery to model membranes. *Eur. J. Pharm Sci.* 2008, 34:203-22). Clinical trials determined that application of ALA-containing cream diminishes facial skin photoaging (Beitner, Randomized, placebo-controlled, double blind study on the clinical efficacy of a cream containing 5% α-lipoic acid related to photoageing of facial skin. *British Journal of Dermatology* 2003, 149:841-849). Unformulated ALA barely penetrates the skin's stratum corneum layer (Podda et al., Kinetic study of cutaneous and subcutaneous distribution following topical application of [7, 8-14c]rac-[alpha]-lipoic acid onto hairless mice. *Biochem. Pharmacol.* 1996, 52:627-633). Water-based, easy-to-use formulations have been prepared using surfactants with nanoparticulate ALA (Ruktanonchai et al., Physicochemical characteristics, cytotoxicity, and antioxidant activity of three lipid nanoparticulate formulations of alpha-lipoic acid. *AAPS PharmSciTech* 2009, 10:227-234) or water-in-oil ALA emulsions supplemented with skin penetration enhancers (Richert et al., Transdermal delivery of two antioxidants from different cosmetic formulations. *Int. J. Cosmetic Sci.* 2003, 25:5-13).

However, despite these and other advances, the need remains for improved lipoic acid agents and methods for their production.

SUMMARY OF THE INVENTION

We have now discovered novel esters of lipoic acid with a variety of different glycerides (mono-, di- or triglycerides). The esters of this invention are generally characterized by Formula 1:

(1)

wherein at least one but no more than two of $R_1$, $R_2$, and $R_3$ are a lipoic acid derivative selected from a lipoate moiety of the formula:

(2)

or a dihydrolipoate moiety of the formula (3)

and the other of the $R_1$, $R_2$, and $R_3$ are independently selected from $C_4$ to $C_{24}$ fatty acid moieties or OH, with the proviso that at least one of the $R_1$, $R_2$, and $R_3$ is a fatty acid moiety. These compounds are readily produced in high yield by a lipase catalyzed transesterification of a glyceride and lipoic acid or an ester thereof.

In accordance with this discovery, it is an object of this invention to provide novel lipoate- or dihydrolipoate-substituted acylglycerols.

It is also an object of this invention to provide a facile and efficacious method of producing the subject lipoate- or dihydrolipoate-substituted acylglycerols by a transesterification reaction.

Another object of the invention to produce lipoate- or dihydrolipoate-substituted acylglycerols which are effective as carriers for lipoic acid.

A further object of the invention to produce lipoate- or dihydrolipoate-substituted acylglycerols which are effective as carriers for lipoic acid for topical and cosmetic applications.

Yet another object of the invention is to produce lipoic acid conjugates that have the advantage of being synthesized from natural materials, while providing a value-added use for vegetable oils.

Other objects and advantages of this invention will become readily apparent from the ensuing description.

DETAILED DESCRIPTION

The compounds lipoyl acylglycerols of the invention are lipoyl acylglycerols and dihydrolipoyl acylglycerols which consist of a glycerol backbone in which one or two of the hydroxyls is substituted with a lipoate moiety or its dihydro derivative, respectively, and the other hydroxyls are substituted with C2-C24 saturated or unsaturated fatty acid moieties. Thus, the fatty acid moiety of formula 1 may be shown as R—C(O)O—, wherein R is a C1 to C23 straight or branched chain hydrocarbon which may be saturated or unsaturated, and may be optionally substituted. Substituted acylglycerols wherein the fatty acid moieties are C4-C24 are preferred (i.e., R is C3-C23), particularly C6-C23 fatty acid moieties (i.e., R is C5-C22). Because most common triglyceride oils are esters composed of C18 and C16 fatty acids, preferred acylglycerols of the invention also include the compounds of formula 1 wherein the fatty acid moieties are selected from oleate (C18:1), stearate (C18), palmitoleate (C16:1), palmitate (C16), and linoleate (C18:2).

As noted above, the substituted acylglycerols of formula (1) may include one or two lipoic acid derivatives of formula (2) or (3). The remainder of the $R_1$, $R_2$, and $R_3$ moieties of the glyceride are independently selected from $C_4$ to $C_{24}$ fatty acid moieties or OH, with the proviso that at least one of is a fatty acid moiety. Thus, compounds contemplated by formula (1) include lipoate- or dihydrolipoate-substituted mono-acylglycerols wherein: one of $R_1$, $R_2$, and $R_3$ is a lipoate or dihydrolipoate, one is an OH and another is a fatty acid moiety; mono-acylglycerols wherein two of $R_1$, $R_2$, and $R_3$ are lipoates or dihydrolipoates and one is a fatty acid moiety; and di-acylglycerols wherein one of $R_1$, $R_2$, and $R_3$ is a lipoate or dihydrolipoate two are fatty acid moieties.

The lipoyl acylglycerol compounds of the invention are most readily produced in a lipase-catalyzed transesterification reaction between a glyceride and lipoic acid. The compounds may be produced from glycerides obtained from a variety of sources, including those of plant, animal or microbial origin. Preferably the glyceride is a triglyceride, particularly a natural vegetable oil, although mono- and diglycerides may be used as well. Exemplary oils include soybean oil, corn oil, pennycress oil, sunflower seed oil, high-oleic sunflower seed oil, canola oil, safflower oil, *cuphea* oil, jojoba oil, coconut oil, palm kernel oil, cottonseed oil, olive oil, peanut oil, castor oil, linseed oil, tung oil, rice oil, *crambe* oil, rape oil and the like, with soybean and corn oil being particularly preferred. These oils may have fatty acid moieties ranging in length from C2-C24, typically from C4-C24, and particularly from C6-C23, and having varying degrees of saturation from completely saturated to tri-unsaturated. Hydroxyl-substituted oils, such as ricinoleic, are also contemplated. Alternatively, animal fats, algal oils and marine oils, including fish and krill oils, may also be used. When the products of the invention are intended for use in cosmetic formulations, it is preferred to select oils that are aromatically pleasing, particularly those having a relatively low level of linolenic acid, for example. Of course, synthetic triglycerides, such as triolein, could also be used as the starting material.

The preferred lipase for use herein is one having regioselective specificity towards the terminal acyl groups of a triglyceride. One such lipase is produced by *Candida antartica*. This enzyme on an inert support is produced by Novo Nordisk (Franklinton, N.C., USA) under the tradename Novozym 435.

The transesterification (glycerolysis) reaction results in the exchange of one or two fatty acids or hydroxides of the glyceride for an equal number of lipoic acid moieties. The reaction is conducted under mild conditions, preferably in the presence of a solvent for the lipoic acid. A variety of solvents may be used, including aliphatic or tertiary alcohols, with t-butanol being preferred. Temperature conditions for the reaction may range from about 20° C. to about 65° C., with the preferred temperatures being in the range of about 55° C. to about 60° C. In laboratory experiments with lipoic acid and triolein (as the triglyceride) in t-butanol solvent at 60° C., the reaction attains equilibrium in approximately 7 days.

Figure 1:
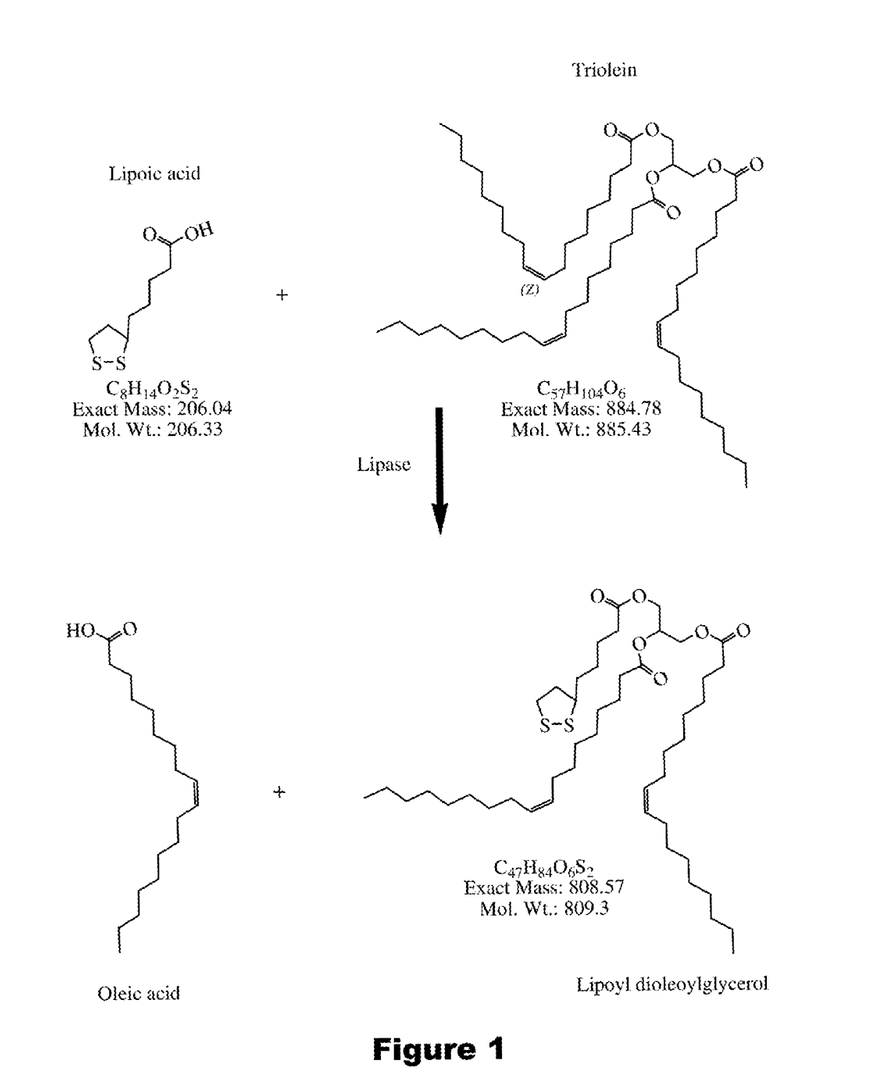
FIG. 1 shows one embodiment of the invention with reaction of lipoic acid with triolein to produce lipoyl dioleoylglycerol (LDOG$_{-SS-}$) as described in Example 1.

FIG. 1 illustrates the transesterification process contemplated by the invention by showing the step involved in the glycerolysis of lipoic acid with triolein to produce lipoyloleins. The figure illustrates the replacement of oleate groups from the triolein with lipoate moieties to form the lipoyl dioleoylglycerol. It is understood that the product is not limited to the lipoyl dioleoylglycerol shown in the figure, and that one or two lipoate moieties may esterify to the glycerol. Moreover, while the lipoic acid esterifies primarily to a terminal carbon of the glycerol, smaller amounts may esterify at the C2 of the glycerol.

Upon completion of the reaction, the accumulated lipoyl acylglycerols may be recovered from the reaction medium. Although formulations of the compounds may be prepared directly from the reaction medium, as a practical matter, it is envisioned that commercial formulations will typically require concentration and preferably substantial purification. Thus, in a preferred embodiment following separation of the solid catalyst, the solvent is removed from the product by heating or evaporation. The product may then purified by extraction with an alcohol such as methanol to separate the lipoyl acylglycerols into a lower, oily phase, followed by further purification by HPLC as described in detail in the Example.

In accordance with an optional embodiment, the lipoyl acylglycerols may be further reacted to prepare a dihydrolipoate-substituted acylglycerol (dihydrolipoyl acylglycerol). This further reaction may be performed following completion of the above-mentioned reaction without isolation of the lipoyl acylglycerols, thereby obviating the need for an intermediate purification step or additional reactors. In this embodiment, the lipoyl acylglycerol prepared above may be reacted with a reducing agent effective for reducing the disulfide of the lipoate to a dithiol. A variety of reducing agents are suitable for use herein, including dithiothreitol, dithioerythreitol, sodium dithionite, and sodium borohydride, with dithiothreitol being preferred. The reaction is also conducted under mild conditions, preferably in the presence of a solvent for the lipoyl acylglycerol. A variety of solvents may be used, with alcohols such as ethanol being preferred. Temperature conditions for the reaction may vary, but room temperature is preferred. The reaction is relatively rapid, and typically reaches equilibrium in approximately 2 hours. The dihydrolipoyl acylglycerol produced may be recovered from the reaction mixture upon completion of the reaction. As above, while formulations of the compounds may be prepared directly from the reaction medium, as a practical matter, it is envisioned that commercial formulations will typically require concentration and preferably substantial purification. Thus, in a preferred embodiment, the solvent is initially removed from the product by heating or evaporation. The product may then purified by extraction with a hydrocarbon such as hexane, followed by filtration and evaporation to separate the dihydrolipoyl acylglycerol into an oil phase which may then be dried.

The lipoyl- and dihydrolipoyl-acylglycerol compounds as defined by formula (1) are particularly suitable for use in skin care applications such as a cosmetic additive or as a skin nutrient. The compounds provide enhanced skin penetration of the lipoic acid, and therefore provide superior performance in the activity of the lipoyl moiety. As noted in Example 1, the dihydrolipoyl acylglycerols serve well as antioxidants in a model membrane system. Topically applied, these molecules may decrease oxidative stress in (epi)dermal tissues, and thereby prevent inflammational processes, age-associated diseases, and delay aging. The lipoyl acylglycerols may also be useful by acting as sources of slow-release lipoic acid. Dermal hydrolytic enzymes would free lipoic acid from the glyceride. The released lipoic acid would then be available to enter the general metabolic pool for use.

The lipoyl- and dihydrolipoyl-acylglycerol compounds of this invention may be formulated into any cosmetic preparations. The cosmetic preparation according to the invention can be formulated as a lotion, cream, gel, stick or aerosol. The base of the formulation may be a water-in-oil emulsion, an oil-in-water emulsion, an oil-in-oil alcohol lotion, a vesicular dispersion, or as an emulsifier-free starch/lipid dispersions as described in U.S. Pat. Nos. 5,676,994 and 5,882,713, both herein incorporated by reference. The term "oil" is used herein to be inclusive of all lipids. The term "lipid" (or fat) is a comprehensive term referring to substances which are found in living cells and which are comprised of only a nonpolar hydrocarbon moiety or a hydrocarbon moiety with polar functional groups (see the Encyclopedia of Chemistry, 3rd Edition, C. A. Hampel and G. G. Hawley, eds., 1973, p. 632, herein incorporated by reference). Most lipids are insoluble in water and are soluble in fat solvents such as ether and chloroform. Commonly used oils for cosmetic formulations include coconut oil, silicone oil and jojoba oil. In a preferred embodiment, the compounds are formulated in lipid or phospholipid vesicles. Briefly, the compounds are mixed with a suitable lipid in a solvent, after which the solvent is removed by drying to yield a film. This film may then be rehydrated in an aqueous buffer, thereby forming liposomes, which typically vary of a range of sizes. Uniform sizes may be obtained by extrusion. Details of a preferred process for producing vesicles are described in the Example.

Because lipoic acid is susceptible to photodegradation, the subject compounds may be optionally formulated with a UV-absorbing agent, particularly for topical applications. A variety of UV-absorbing agents are suitable for use herein, including ferulic acid or other UVA and UVB sunscreen agents, such as 2-phenyl-benzimidazole-5-sulfonic acid, TEA salicylate, octyl dimethyl PABA, padimate-O (2-ethylhexyl 4-(dimethylamino)benzoate) and octyl methyl cinnamate. Other optional components which may be included in the formulation include, but are not limited to inorganic physical sunblocks, such as zinc oxide and $TiO_2$; artificial tanning agents; abrasives; absorbents; fragrances; pigments; colorings/colorants; essential oils; skin sensates; astringents carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like. Suitable emulsifiers include any of those conventionally used for cosmetic formulations, including, for example, ethoxylated esters of natural derivatives, such as polyethoxylated esters of hydrogenated castor oil, a silicone oil emulsifier such as silicone polyol, free or ethoxylated fatty acid soap, an ethoxylated fatty alcohol, a free or ethoxylated sorbitan ester, an ethoxylated fatty acid or an ethoxylated glyceride. Exemplary agents and additives that could be included in formulations, as well as suggested levels of addition, are given in U.S. Pat. No. 5,989,528 (Tanner et al.), which is herein incorporated by reference.

The following example is intended only to further illustrate the invention and is not intended to limit the scope of the invention which is defined by the claims.

Example 1

Figure 2:
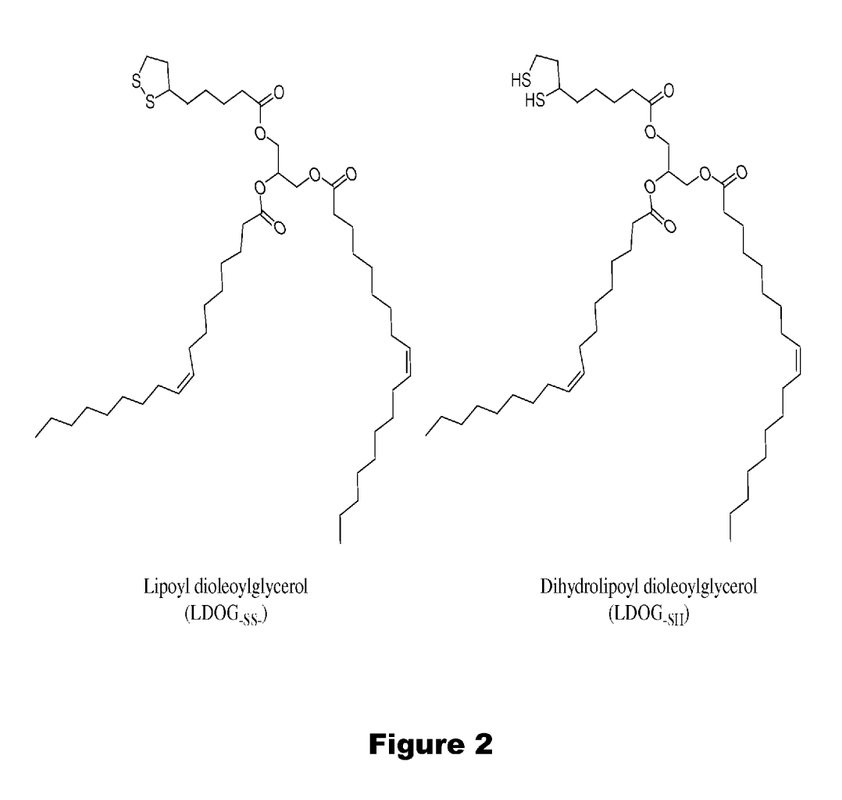
FIG. 2 shows the structures of lipoic glycerides lipoyl dioleoylglycerol and its dihydro-derivative, dihydrolipoyl dioleoylglycerol (LDOG$_{-SH}$), as described in Example 1.

In this Example, the lipoic acid derivative lipoyl dioleoylglycerol ($LDOG_{-SS-}$) was enzymatically prepared and examined for its potential to serve as an antioxidant in liposomal vesicles. $LDOG_{-SS-}$ (disulfide form) and dihydrolipoyl dioleoylglycerol ($LDOG_{-SH}$, dithiol form), depicted in FIG. 2, were incorporated into large, unilamellar vesicles of dioleoylphosphatidylcholine (DOPC). The physical integrity and antioxidant capacity of the $LDOG_{-SS-}/LDOG_{-SH}$-doped DOPC vesicles in physiologic conditions were assessed. The orientation of the $LDOG_{-SS-}$ and $LDOG_{-SH}$ sulfur groups within the membrane bilayer were investigated using molecular mechanics modeling.

Materials and Methods

Reagents and Materials. R/S α-lipoic acid, triolein, DL-dithiothreitol, t-butanol, cobalt (II) chloride hexahydrate, ethylenediaminetetraacetic acid disodium dehydrate (EDTA), 2,2'-azobis(2-amidinopropane)dihydrochloride (AAPH), and hexane were purchased from Sigma-Aldrich. Novozym 435 was obtained from Novozymes A/S. Ethanol (200 proof) was purchased from Decon Laboratories, Inc. (King of Prussia, Pa.). Supercritical Fluid Chromatography (SFC)/Supercritical Fluid Extraction (SFE) grade $CO_2$ was purchased from Airgas Products Co. (Radnor Township, Pa.). 1,2-Dioleoyl-sn-glycero-3-phosphocholine (DOPC) was bought from Avanti Polar Lipids (Alabaster, Ala.). High purity calcein, 4,4-difluoro-5-methyl-4-bora-3a,4a-diaza-s-indacene-3-dodecanoic acid (Bodipy® 500/510 C1, C12 or C1,C12-Bodipy), 5-butyl-4,4-difluoro-4-bora-3a,4a-diaza-s-indacene-3-nonanoic acid (Bodipy® 500/510 C4 C9 or C4,C9-Bodipy), 4,4-difluoro-5-octyl-4-bora-3a,4a-diaza-s-indacene-3-pentanoic acid (BODIPY® 500/510 C8,C5 or C8,C5-Bodipy), and 4,4-difluoro-5-(4-phenyl-1,3-butadienyl)-4-bora-3a,4a-diaza-s-indacene-3-undecanoic acid ($C_{11}$-Bodipy® 581/591) were purchased from Invitrogen (Carlsbad, Calif.). Potassium phosphate monobasic, potassium phosphate dibasic, Sephadex G-75 column beads, columns and sodium chloride were obtained from Fisher Scientific.

Preparation of Lipoyl Dioleoylglycerol. To prepare $LDOG_{-SS-}$, ALA (2.0 g), triolein (9 g), t-butanol (4 g) and immobilized *Candida antarctica* lipase B (1.5 g Novozym 435) were combined and shaken at 60° C. for one week. t-Butanol was removed from the reaction product by rotary evaporation at 60° C. The product was extract with methanol twice (1:2 product to methanol) in a separatory funnel, and the lower oily phases were combined. This $LDOG_{-SS-}$-containing oil was subjected to further purification by HPLC using a Luna semi-preparative phenylhexyl column (250 mm×10 mm, 10 μm; Phenomenex, Torrance, Calif.) developed with 95% acetonitrile/5% acetone at a flow rate of 5 mL/min, collecting 1.25 mL fractions (UV detection at 340 nm). Fractions containing $LDOG_{-SS-}$ were reduced in volume and combined, and then chromatographed again on the phenylhexyl column developed with methanol. Combined LDOG fractions were freed of methanol under vacuum and then stored frozen until use. LDOG was an oil at room temperature, and pure by HPLC and NMR (see Electronic Supplementary Information). $^1$H NMR ($d_6$-acetone, 500 MHz): δ (ppm) 5.36 (4H, m, 2-$CH_2CH=CHCH_2$), 5.25 (1H, m, $CHO(CH_2O)_2$), 4.1-4.4 (4H, dm, $\overline{2}$-$CH_2O$), 3.64 (1H, m, $SCH(\overline{CH_2})_2$), 3.10-3.25 (2H, dm, $SCH_2CH_2$), 2.50 and 1.93 (2$\overline{H}$, m, $SCH_2CH_2CH$), 2.35 (m, 3-$C\overline{H}_2CH_2CO_2$), 2.06 (m, 2-$(CH_2CH_2)_2C\overline{H}=CH$), 1.63 (m, 4-$C\overline{H}_2CH_3CH=CH$), 1.32 (m, $\overline{CH_2}CH_2CH_2$), 0.90 (6H, t, 2-$C\overline{H_3}$). $^{13}$C NMR ($d_6$-acetone): δ (pp$\overline{m}$) 172.3 ($CH_2CH_2CO_2$), 129.6 (CH=CH), 69.1 ($CH(CH_2O—)_2$), 61.9 ($C\overline{H}(CH_2O—)_2$), 56.3 (S $CH(CH_2)_2$), 40.0 ($SCH_2CH_2CH$), 38.2 ($SCH_2CH_2$), 34.5-22.4 (aliphatic), 13.6 ($C\overline{H_3}$—). Electrospray ionization mass spectroscopy (ESI-MS): 831.57 $[M+Na]^+$ (calcd $C_{47}H_{84}O_6S_2$: 808.57).

Preparation of Dihydrolipoyl Dioleoylglycerol ($LDOG_{-SH}$). $LDOG_{-SS-}$ (100.4 mg, 0.119 mmol) was dissolved in ethanol (5 mL, 85.6 mmol) to form a light yellow solution. Dithiothreitol (1.00 g, 6.5 mmol) was added to the solution and dissolved within 5 min. The solution was stirred at room temperature for 2 h. Subsequently, the ethanol was removed by rotoevaporation and the resultant residue was extracted with two 10-mL fractions of hexane. The hexane extract was filtered four times through 13-mm diameter, 0.45-μm pore size PVDF Pall Acrodisc syringe filters. The hexane filtrate was rotoevaporated to dryness to yield a pale yellow oil. The oil was dried in vacuo at room temperature for 18 h. Yield, 24.6 mg.

The reduction of $LDOG_{-SS-}$ was monitored by supercritical fluid chromatography SFC using a Selerity Technologies, Series 4000 chromatograph. Samples (100 μL) taken from the reduction reactions were diluted in 1.0 mL of ethanol and 10 μL used for injection. The samples were developed with $CO_2$ on a Selerity Technologies SB-methyl-100 SFC column (PN AE002, 50 μm×10 m×0.25 μm film) starting at 100 atm and 100° C. The starting pressure was held for 5 min and ramped at 15 atm/min to a final pressure of 310 atm, which was held for 11 min. The column temperature was isothermal for the duration of the analysis. The FID was set at 350° C. Under these analytical SFC conditions dithiothreitol, $LDOG_{-SS-}$ and $LDOG_{-SH}$ resulted in $R_t$ of 9.16, 17.07, and 17.43 min, respectively.

Lipid Preparation and Formation of Unilamellar Phospholipid Vesicles. Lipid mixtures and vesicles were prepared as described previously (Laszlo et al. 2010. ibid). Lipids were prepared from appropriate amounts of DOPC in chloroform and $LDOG_{-SS-}$ or $LDOG_{-SH}$ (at 1- or 5-mol % of total lipids) in ethanol added to clean amber vials and then gently mixed. Solvents were removed under a stream of argon and then vacuum. The dried lipids were rehydrated in the appropriate buffer and mixed periodically to form multilamellar phospholipid vesicles. The vesicles were subjected to freeze-thaw cycles and then extrusion to form unilamellar vesicles (approx. 125 nm in diameter). Vesicles were covered with argon, protected from light and stored at 4° C. until used. DOPC vesicles incorporating 1- or 5-mol % ALA or DHLA were similarly produced.

Vesicle Leakage (Calcein-Cobalt). Vesicles with and without LDOG were evaluated for membrane integrity using a leakage assay described previously (Evans. Room-temperature ionic liquid cations act as short-chain surfactants and disintegrate a phospholipid bilayer. *Colloid. Surface. A* 2006, 274:11-17; and Laszlo et al. 2010. ibid). Briefly, the leakage assay was designed such that the low fluorescent signal of the entrapped calcein-cobalt complex increased as vesicles leaked their contents and cobalt was stripped from calcein by external EDTA. Vesicle leakage was monitored with a fluorometer. Samples were continuously stirred in 1-cm path length quartz cuvettes 37° C., with measurements taken for 30 min at 5-s intervals. Experiments were conducted in triplicate. Leakage percentage (L) was determined from the intensity of the fluorescent signal, $100\times(F_t-F_o)/(F_{max}-F_o)$, where $F_t$ was the fluorescent signal over time, $F_o$ was the extrapolated initial signal at time zero, and $F_{max}$ was the fluorescent signal at the end of the experiment after rupture by addition of Triton X-100 solution. The apparent rate constant k ($ms^{-1}$) and maximum extent of vesicle leakage ($L_\infty$), prior to vesicle rupture, were obtained by fitting to the equation: $L_t=L_\infty(1-\exp(-kt))$.

Lipid Oxidation Inhibition. Lipid oxidation inhibition by LDOG was measured by the lipid peroxidation inhibition capacity assay, which employs AAPH as a free-radical initiator and the lipidic reporter molecule $C_{11}$-Bodipy (Zhang et al., Lipid peroxidation inhibition capacity assay for antioxidants based on liposomal membranes. *Mol. Nutr. Food Res.* 2006, 50:714-724). $C_{11}$-Bodipy fluoresces at 595 nm until it is oxidized, at which point its fluorescence shifts to ~520 nm (Drummen et al., C11-bodipy581/591, an oxidation-sensitive fluorescent lipid peroxidation probe: (micro)spectroscopic characterization and validation of methodology. *Free Radical Biol. Med.* 2002, 33:473-490). Conditions for the assay using modified glycerides have been detailed previously (Laszlo et al. 2010. ibid). DOPC and $C_{11}$-Bodipy were combined in a vial, dried to a film, and then rehydrated in 20 mM Tris-HCl, pH 7.4. When included, ALA, DHLA, $LDOG_{-SS-}$, or $LDOG_{-SH}$ (at 1- or 5-mol % of total lipids) in ethanol were added prior to formation of vesicles. Unilamellar vesicles were prepared from rehydrated lipids as described above. Samples were diluted to a final concentration of 2.5 mM DOPC (2.4 μM $C_{11}$-Bodipy) and allowed to equilibrate to 37° C. for 15 min prior to the introduction of AAPH. From the time of AAPH addition (40 mM final concentration), fluorescence intensity (excitation at 540 nm, emission at 595 nm) was measured every minute for 180 min. Experiments were conducted in triplicate at least. The relative fluorescence intensity was calculated by dividing the reading at each minute by the initial fluorescence at the beginning of the experiment ($F_t/F_o$). Background subtraction was accomplished using the appropriate vesicles without $C_{11}$-Bodipy.

The water-soluble antioxidant Trolox was used for comparison. Trolox was combined with DOPC and $C_{11}$-Bodipy, dried, and then rehydrated as described above. A final Trolox concentration range of 10 to 125 μM was employed. The peroxyl radical scavenging capacity of the test antioxidant relative to Trolox (i.e., the relative antioxidation activity) was calculated using the following equation $$= \frac{(AUC_{Sample} - AUC_0)}{(AUC_{Trolox} - AUC_0)} \times \frac{mol_{Trolox}}{mol_{Sample}}, \quad (1)$$

where $AUC_{Sample}$ is the area under the fluorescence curve (AUC) for vesicles containing antioxidant, $AUC_{Trolox}$ is the area under the curve for vesicles containing 50 μM Trolox (thereby arbitrarily assigned a relative antioxidation activity value of 1.0), $AUC_0$ is the area under the curve for vesicles containing only $C_{11}$-Bodipy, and $mol_{Sample}$ is the molar concentration of the antioxidant (Naguib, A fluorometric method for measurement of peroxyl radical scavenging activities of lipophilic antioxidants. *Anal. Biochem.* 1998, 265:290-298). The AUC was calculated from the average of three different methods, those described by Cao and coworkers (Cao et al., Oxygen-radical absorbance capacity assay for antioxidants. *Free Radical Biol. Med.* 1993, 14:303-311), Naguib (Naguib, Antioxidant activities of astaxanthin and related carotenoids. *J. Agric. Food. Chem.* 2000, 48:1150-1154), and Zhang and coworkers (Zhang et al. 2006. ibid).

Lipoic Moiety Location Using Bodipy-Labeled Fatty Acid. Prior studies determined drug location within phospholipid membrane using a series of n-(9-anthroyloxy) stearic acids (Ferreira et al., Partition and location of nimesulide in epc liposomes: A spectrophotometric and fluorescence study. *Analytical and Bioanalytical Chemistry* 2003, 377:293-298; and Ferreira et al., Effects of diclofenac on epc liposome membrane properties. *Anal Bioanal Chem* 2005, eFIRST) in which the anthroyloxy moiety is inserted at the 2, 6, 9, or 12 carbon position on the fatty acid chain. Fluorescence quenching of the anthroyloxy moiety in the presence of increased quencher concentrations was used to infer quencher position within the bilayer. This is based on the concept that quenching occurs between the anthroyloxy group and the nearest quencher only. In this current study, the membrane location of the lipoic moiety of $LDOG_{-SS-}$ and $LDOG_{-SH}$ was similarly determined using a fatty acid labeled with Bodipy® 500/510 located at different positions of the fatty acid. The Bodipy® 500/510 probes were: $C_1,C_{12}$-Bodipy, in which the Bodipy group is 12-carbons away from the carboxyl group of dodecanoic acid and has one carbon attached on the opposite end, $C_4,C_9$-Bodipy, in which the probe is nine carbons away from the carboxyl group of nonanoic acid and has four carbons attached on the opposite end, and $C_8,C_5$-Bodipy, wherein the Bodipy group resides five carbons away from the carboxyl group of pentanoic acid and has eight carbons attached on the opposite end. Lipids were dried at 950 μM with 1 μM probe and 0, 10, 30 or 50 μM $LDOG_{-SS-}$ or $LDOG_{-SH}$. Lipids were hydrated in PBS buffer, from which vesicles were formed as described above. Fluorescence emission spectra were recorded using 509 nm excitation. Relative fluorescence ($F/F_0$) was determined, where $F_0$ was the fluorescence value at 517 nm for vesicles without any lipoyl lipid present and F was the 517 nm emission peak value of vesicles with either lipoyl lipid present. Measurements were conducted in quadruplicate.

Molecular Modeling. Theoretical calculations were carried out using HyperChem v8.0.9 package (Hypercube Inc. Gainesville, Fla.) and Parallel Quantum Solutions v3.2 software (PQS, Fayetteville, Ark.). The initial structures of $LDOG_{-SH}$, $LDOG_{-SS-}$, Bodipy-5, Bodipy-9, Bodipy-12, DOPC were built using the PM3 semi-empirical method in vacuo and the Polak-Ribiere conjugate gradient method with the RMS gradient of 0.01 kcal $mol^{-1}$. The DOPC membrane was built based on disordered DOPC structures generated by ten consecutive 1-ps molecular dynamics experiments using the Charmm27 force field on the PM3 geometry optimized structure of DOPC. The triacylglycerol moiety for the DOPC structure was modeled based on structures of dimyristoyl phosphatidylcholine previously studied using density functional theory augmented with a damped dispersion energy term (Krishnamurty et al., Density functional theory-based conformational analysis of a phospholipid molecule (dimyristoyl phosphatidylcholine). *J. Phys. Chem. B* 2008, 112:13433-13442). The calculations were carried out in vacuo with a bath relaxation time was 0.1 picoseconds at 298.15 K. The DOPC lipid bilayer (35×40×45 Å) was built using the results of the molecular dynamic simulations. Geometry optimization calculations of the DOPC membrane and the probes or LADOG derivatives were performed using the Charmm27 empirical force field and Polak-Ribiere conjugate gradient method with the RMS gradient of 0.01 kcal $A^{-1}$ $mol^{-1}$.

Results and Discussion

Figure 3:
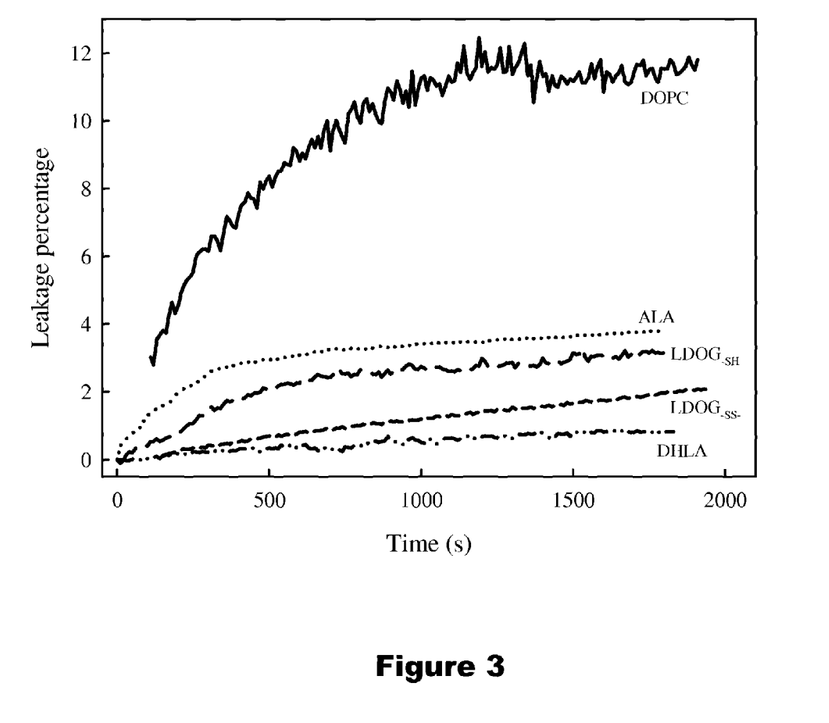
FIG. 3 shows Time dependence of calcein-cobalt leakage from DOPC vesicles and DOPC vesicles augmented with 5-mol % of lipoic acid (ALA), lipoyl dioleoylglycerol (LDOG$_{-SS-}$), dihydrolipoic acid (DHLA), or dihydrolipoyl dioleoylglycerol (LDOG$_{-SH}$). Data represent the mean values of 3-6 experiments in Example 1.

Vesicle Stability. The effect of $LDOG_{-SS-}$ and $LDOG_{-SH}$ on phospholipid vesicle stability was explored by monitoring calcein-cobalt leakage from the DOPC vesicle inner aqueous phase. ALA and DHLA-enriched vesicles were examined for comparison. FIG. 3 exhibits the leakage of DOPC vesicles at 37° C. with four lipoic species (ALA, DHLA, $LDOG_{-SS-}$ and $LDOG_{-SH}$). Two attributes of vesicle leakage can be discerned (reflecting compositional influences on membrane fluidity and liposome defects). There was a first order release of calcein-cobalt that rose to a plateau. This release profile was modeled with an apparent rate constant k and pseudo-equilibrium maximum leakage value $L_\infty$. $L_\infty$ was a small percentage of the total entrapped calcein for all vesicle formulations (Table 1). Vesicles containing either $LDOG_{-SS-}$ or $LDOG_{-SH}$ leaked significantly less than vesicles without them, based on $L_\infty$ values. Leakage rates were lowered an order of magnitude by the inclusion of $LDOG_{-SS-}$, however this trend was not sustained by $LDOG_{-SH}$. This observation indicated that dithiolane/dithiol groups differentially interact with membrane phospholipids. In contrast, ALA did not cause the vesicles to leak more slowly than the control DOPC vesicles, although the maximum leakage was significantly less than that of unaugmented liposomes. Therefore the release profiles of ALA- and $LDOG_{-SH}$-doped DOPC liposomes were similar. Incorporation of DHLA lead to the lowest amount of vesicle leakage among the samples examined. The effect of DHLA on leakage rates was unclear at the 1-mol % amount due to a high dispersion in the data, but at a 5-mol % DHLA inclusion level it was apparent that leakage rates were five-fold lower than those of unaugmented liposomes.

Based on calcein leakage rates, vesicle stability increased as: DOPC, ALA<$LDOG_{-SH}$, DHLA<$LDOG_{-SS-}$. Maximum leakage amounts however indicated stability increased as: DOPC<ALA, $LDOG_{-SH}$, $LDOG_{-SS-}$<DHLA. Measures of liposome stability by the calcein leakage technique are routinely reported in terms of leakage rates or maximum leakage amounts. Either parameter seems sufficient to identify trends among different treatments, although with the materials examined herein it is evident that there is not an exact correlation between the two parameters. We are not aware of literature explaining the specific physical phenomenon, such as temporary pore formation or vesicle fusion, that would account for the lack of strict parameter correlation.

DOPC vesicles are in a liquid-crystalline phase at 37° C. The neutral nature of the membrane minimizes the electrostatic interaction of negatively charged calcein with the phospholipid headgroup. Therefore, calcein permeation rates across these membranes correlate with membrane fluidity (Shimanouchi et al., Calcein permeation across phosphatidylcholine bilayer membrane: Effects of membrane fluidity, liposome size, and immobilization. *Colloid. Surface. B* 2009, 73:156-160). Interactions with some small molecules can cause membrane disruption and vesicle fusion, which results in high leakage values (Środa et al., Genistein derivatives decrease liposome membrane integrity—calcein release and molecular modeling study. *Biophys. Chem.* 2008, 138:78-82; and Chen et al., Destabilization of artificial biomembrane induced by the penetration of tryptophan. *Appl. Surf. Sci.* 2011, 257:5070-5076). None of the lipoic species of the present study caused such liposomal destruction. Certain carotenoids and cyclic terpenoids are known to stabilize liposomes (Han et al., Oleanolic acid and ursolic acid stabilize liposomal membranes. *Lipids* 1997, 32:769-773; and Hara et al., Stabilization of liposomal membranes by thermozeaxanthins: Carotenoid-glucoside esters. *BBA-Biomembranes* 1999, 1461:147-154). This appears to be the case as well for $LDOG_{-SH}$ and $LDOG_{-SS-}$. It is likely that their presence in liposomes increased lipid packing density. In an early study (Laszlo et al. 2010. ibid), we demonstrated that a monophenolic counterpart to the present study lipids, feruloyl dioleoylglycerol, did not modify DOPC vesicle leakiness. All are composed of two oleoyl groups esterified to glycerol; the only difference being the presence of lipoic or ferulic groups (>90% in the sn-1 or sn-3 position). This comparison suggests that differences in packing density may be specifically ascribed to the effect of the lipoyl group. The molecular modeling studies described below were undertaken in part to explore further how $LDOG_{-SH}$ and $LDOG_{-SS-}$ orient within the membrane and may exert their influence on membrane stability. The dramatically different effects on membrane stability of ALA and DHLA will be explored in a separate communication.

Figure 4:
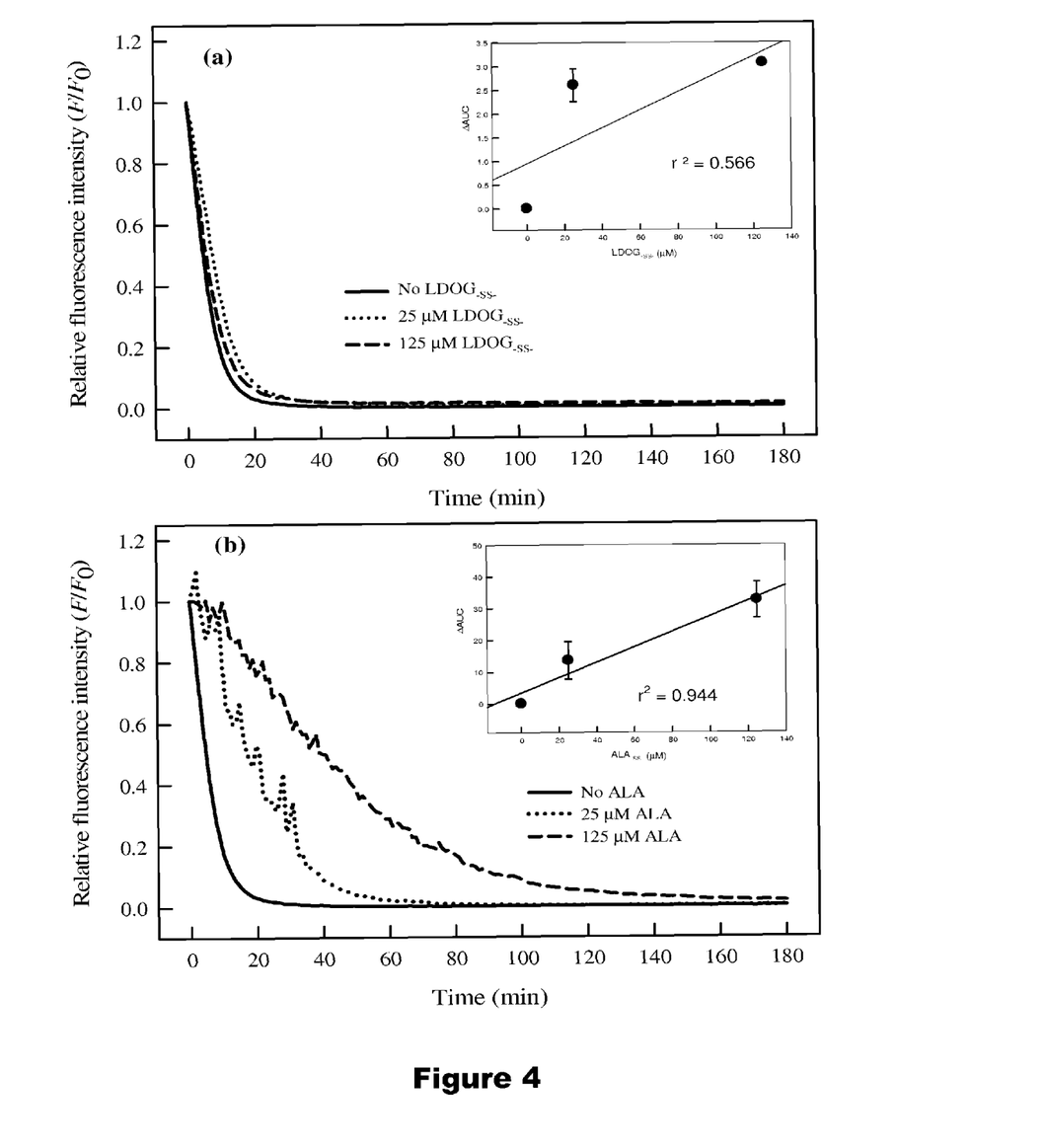
FIG. 4 shows the lipid peroxidation inhibition by (a) LDOG$_{-SS-}$ and (b) ALA in DOPC vesicles at 37° C. The insert displays the net area under the curve (ΔAUC) versus concentration in Example 1.
Figure 5:
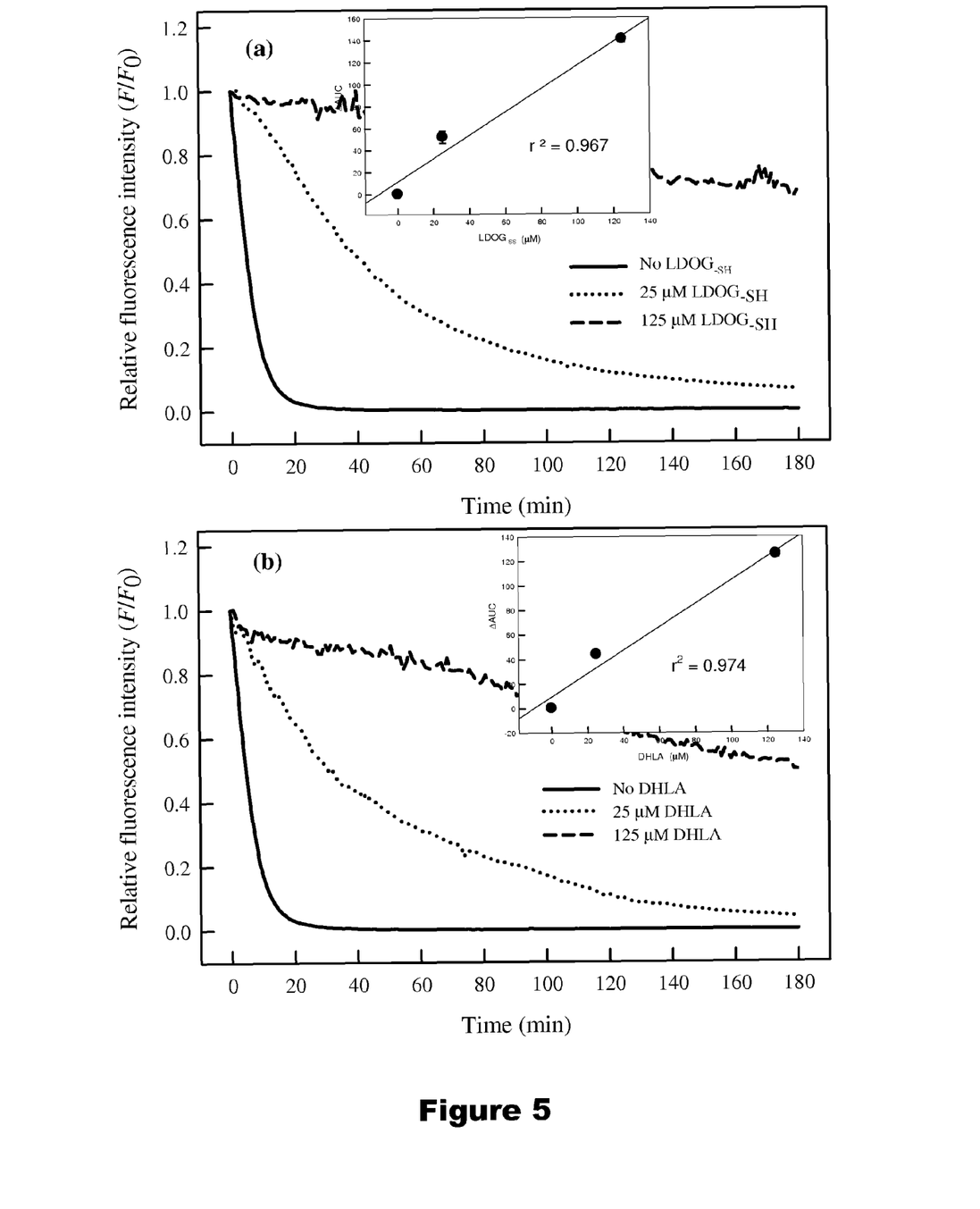
FIG. 5 shows the lipid peroxidation inhibition capacity of (a) LDOG$_{-SH}$ and (b) DHLA in DOPC vesicles at 37° C. The insert displays the net area under the curve (ΔAUC) versus concentration in Example 1.

Lipid Peroxidation Inhibition. The performance of $LDOG_{-SS-}$ and $LDOG_{-SH}$ as antioxidants in a model membrane environment was examined by subjecting phospholipid vesicles containing these molecules to oxidative conditions using AAPH, a free-radical generator. Fluorescent $C_{11}$-Bodipy served as the reporter of lipid oxidation within the vesicles. Vesicles containing ALA, DHLA, or Trolox were examined for comparison. In the absence of antioxidant, fluorescence from $C_{11}$-Bodipy-doped DOPC vesicles rapidly declined, reflecting the rapid oxidation of the probe by AAPH radicals (FIG. 4). It is apparent that the AAPH radical is able to partition from the aqueous phase to the hydrophobic center of the membrane. $LDOG_{-SS-}$ afforded little oxidation protection to the vesicles (FIG. 4a). This indicates that $LDOG_{-SS-}$ is unreactive with AAPH peroxy radicals. In contrast, inclusion of $LDOG_{-SH}$ into the vesicles markedly extended the probe's fluorescent period (FIG. 5a), indicative of the presence of a strong antioxidant. $LDOG_{-SH}$ inhibited vesicle lipid oxidation in a concentration-dependent fashion (FIG. 5a insert). Table 2 summarizes the antioxidant capacities of the various lipoic acid entities in comparison to Trolox. As expected, the reduced (dithiol) species (DHLA and $LDOG_{-SH}$) exhibited the highest antioxidant capacities. These two molecules displayed antioxidant capacities double that of Trolox at the same concentration. The general trend in decreasing antioxidant effectiveness was $LDOG_{-SH}$>DHLA>Trolox>ALA>$LDOG_{-SS-}$. There was therefore a huge disparity between $LDOG_{-SS-}$ and $LDOG_{-SH}$ in their ability to scavenge the AAPH radical in a membranous environment. The different antioxidant capability of $LDOG_{-SS-}$ and $LDOG_{-SH}$ may be due to their different redox states. The disulfide redox couple is 1.1 V, while the sulfhydryl redox couple is −0.32 V (Bonifačić and Asmus, One-electron redox potentials of rssr+.-rssr couples from dimethyl disulphide and lipoic acid. *J. Chem. Soc., Perkin Trans.* 2 1986, 1805-1809; and Ghibu et al. 2009. ibid).

It is possible to compare the antioxidant capacity of lipoic species with a variety of phenolic compounds. Most closely related is the previously characterized feruloyl dioleoylglycerol (Laszlo et al. 2010. ibid). The capacity of this highly lipophilic monophenol was found to be slightly less than that of monophenolic Trolox. Therefore, $LDOG_{-SH}$ is the more effective triglyceride antioxidant. The protective effect of $LDOG_{-SH}$ is comparable to polyphenolic gallate esters and flavonoids (Zhang et al. 2006. ibid).

Membrane packing density is known to influence the oxidative stability of polyunsaturated fatty acyl esters in liposomes (Henna et al., Oxidative stability of marine phospholipids in the liposomal form and their applications. *Lipids* 2011, 46:3-23). The vesicle leakage results given above indicated that DHLA and $LDOG_{-SH}$ (at 5-mol % incorporation) increased phospholipid packing. The tighter packing may have contributed to their antioxidant effectiveness because free radicals would have less access to the oxidation probe.

Figure 6:
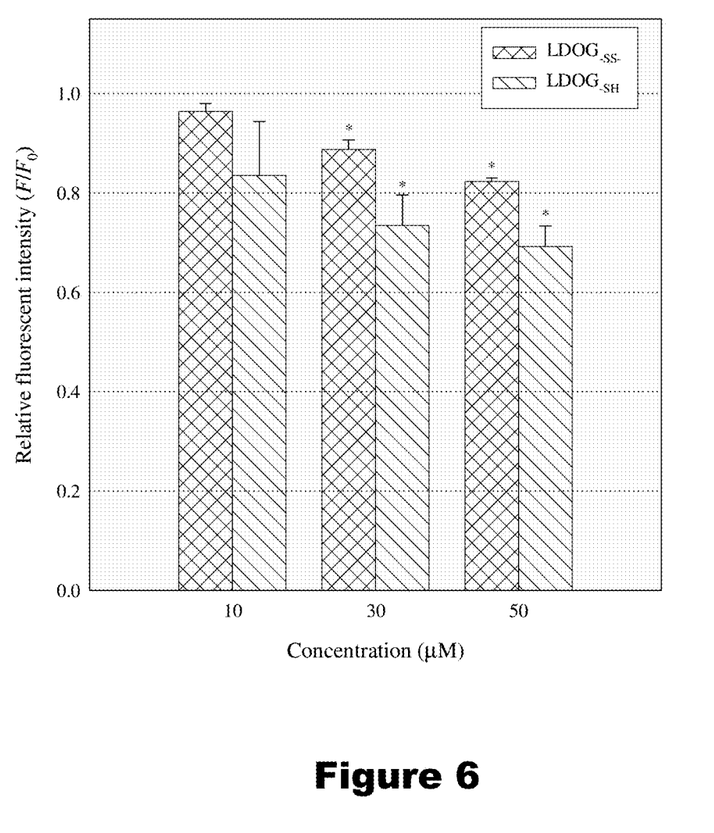
FIG. 6 shows the quenching of $C_8$,$C_5$-Bodipy fluorescence at increasing concentrations of LDOG$_{-SS-}$ and LDOG$_{-SH}$ in DOPC vesicles. The vesicle concentration was 950 μM in each experiment. Fluorescent intensities (F) were normalized with unaugmented DOPC vesicle values ($F_0$). Asterisks indicate values significantly less than 1.0 (P<0.05) in Example 1.

Membrane Location of Lipoyl Moiety. The calcein leakage results indicated that $LDOG_{-SS-}$ and $LDOG_{-SH}$ stabilized liposomes, perhaps by altering membrane phospholipid packing density through some interaction with the lipoyl moieties of these molecules. To better understand this effect, fluorescence quenching of Bodipy-labeled fatty acids by $LDOG_{-SS-}$ and $LDOG_{-SH}$ was measured to determine the accessibility of each lipoyl moiety to the probes. Each probe located the Bodipy reporter group to a different depth within the membrane. The most shallow probe, $C_8,C_5$-Bodipy, was the only one quenched by either lipoyl lipid. FIG. 6 shows that the fluorescence of $C_8,C_5$-Bodipy decreased moderately as the concentration of either lipoyl molecule increased in the membrane, as would be expected for a weakly interacting quencher. From this finding it can be inferred that the dithiolane and dithiol moieties of the triglycerides reside in close proximity to the hydrophilic/lipophilic interfacial region of the bilayer. A similar conclusion was reached regarding the feruloyl moiety of feruloyl dioleoylglycerol (Laszlo et al. 2010. ibid). Thus, the antioxidant portion of these molecules is poised to react with reactive oxygen species approaching the membrane from the aqueous phase. That lipoyl groups altered membrane stability, while the feruloyl moiety did not do so, indicated antioxidant membrane location may not be a determinant of vesicle stability.

Computational analysis. A portion of the DOPC membrane bilayer was modeled to gain insight into the nature of the $C_8,C_5$-, $C_4,C_9$-, $C_1,C_{12}$-Bodipy probes, $LDOG_{-SH}$ and $LDOG_{-SS-}$, within the bilayer. The results of geometry optimization calculation showed that the carboxylic acid moiety of the Bopidy probes resides in the region of the DOPC bilayer with the charged headgroup. The depth of the fluorophore moiety of the Bodipy probe in the bilayer is dependent on the position of the probe moiety within the long alkyl chain. The fluorophore 4,4-difluoro-4-bora-3a,4a-diaza-s-indacene moiety of $C_8,C_5$-Bodipy is embedded near the headgroups of the DOPC membrane bilayer while the fluorophore moieties of $C_4,C_9$-Bodipy and $C_1,C_{12}$-Bodipy are positioned progressively deeper into the hydrophobic chain region in the membrane model. These results correspond with our experimental studies that show these molecules probe different locations within the membrane and support the concept that the proximal location of the dithiolane and dithiol moieties of $LDOG_{-SH}$ and $LDOG_{-SS-}$ is the hydrophilic/lipophilic interfacial region of the bilayer, based on their sole interaction with $C_8,C_5$-Bodipy.

The interaction of $LDOG_{-SH}$ in the DOPC membrane. $LDOG_{-SS-}$ was similarly situated. A low-energy, stable conformation places the dithiol groups at the hydrophilic/lipophilic interface with oleoyl chain extended into the hydrophophic region and spanning both leaflets of the DOPC lipid bilayer. The splayed structure of $LDOG_{-SS-}$ and $LDOG_{-SH}$ are very similar to that of FDOG in membranes (Laszlo et al. 2010. ibid). It is expected that having the antioxidant positioned at the membrane hydrophilic/lipophilic interface improves the likelihood that radicals generated in the aqueous phase are intercepted prior to reaching oxidation-sensitive acyl chain double bonds.

Lipoic acid is subject to photodegradation, resulting in a loss of physiological activity (Wada et al., The effect of biothiol on uv irradiated α-lipoic acid. *BioFactors* 2008, 34:285-292). It would thus make sense to couple a UV-absorbing molecule such as ferulic acid to lipoic acid in topical formulations. The question of whether conjoining these two molecules to the same glycerol molecule would provide greater photostability than a simple mixture of the two entities awaits examination.

Our observations suggest that $LDOG_{-SH}$ serves well as an antioxidant in a model membrane system. Topically applied, these molecules may decrease oxidative stress in (epi)dermal tissues, and thereby prevent inflammatory processes, age-associated diseases, and delay aging. $LDOG_{-SS-}$ may also be useful by acting as a source of slow-release lipoic acid. Dermal hydrolytic enzymes would free lipoic acid from the glyceride. The released lipoic acid would then be available to enter the general metabolic pool for use.

TABLE 1

Leakage properties of DOPC vesicles with incorporated ALA, DHLA, LDOG__SS__, or LDOG__SH

| antioxidant | antioxidant amount (mol %) | leakage rate constant[a] (ms$^{-1} \cdot 10^3$) | maximum leakage[b] (%) |
|---|---|---|---|
| none | — | 2.60 ± 0.52 | 11.8 ± 3.3 |
| ALA | 1 | 5.19 ± 1.32 * | 7.6 ± 2.1 |
| ALA | 5 | 3.98 ± 1.69 | 4.7 ± 0.7 |
| DHLA | 1 | 1.43 ± 1.25 | 0.7 ± 0.3 |
| DHLA | 5 | 0.48 ± 0.05 * | 1.5 ± 0.6 |
| LDOG__SS__ | 1 | 0.43 ± 0.12 * | 4.2 ± 0.7 |
| LDOG__SS__ | 5 | 0.31 ± 0.06 * | 3.6 ± 0.5 |
| LDOG__SH__ | 1 | 4.90 ± 0.90 * | 6.1 ± 0.5 |
| LDOG__SH__ | 5 | 1.88 ± 0.01 | 3.1 ± 0.2 |

[a] Leakage rate constant reported as the mean and standard deviation of determinations conducted in triplicate at least. One-way ANOVA (Dunnett's method) was applied to the data. Items marked with an asterisks are considered to be statistically different ($P < 0.05$) from the control (no antioxidant) sample.
[b] $L_\infty$ obtained by fitting to the equation: $L_t = L_\infty (1 - \exp(-kt))$. All treatments were statistically different ($P < 0.05$) from the control (no antioxidant) group.

TABLE 2

Relative antioxidant capacity of Trolox and lipoic species in the lipid peroxidation inhibition assay

| antioxidant | concentration (μM) | relative antioxidant capacity[a] |
|---|---|---|
| Trolox | 10 | 0.98 ± 0.28 |
| Trolox | 25 | 0.80 ± 0.09 |
| Trolox | 50 | 1.00 |
| Trolox | 125 | 0.80 ± 0.08 |
| ALA | 25 | 0.61 ± 0.26 |
| ALA | 125 | 0.29 ± 0.05 * |
| DHLA | 25 | 1.95 ± 0.03 * |
| DHLA | 125 | 1.12 ± 0.02 * |
| LDOG__SS__ | 25 | 0.09 ± 0.01 * |
| LDOG__SS__ | 125 | 0.02 ± 0.002 * |
| LDOG__SH__ | 25 | 2.46 ± 0.10 * |
| LDOG__SH__ | 125 | 1.21 ± 0.04 * |

[a] Relative antioxidant activity reported as the mean and standard deviation of values calculated according to Equation 1. Experiments were conducted in triplicate at least. Values are relative to 50 μM Trolox. One-way ANOVA (Dunnett's method) was applied to the data. Items marked with an asterisks are considered to be statistically different ($P < 0.05$) from the control (25 or 125 μM Trolox) sample.

It is understood that the foregoing detailed description is given merely by way of illustration and that modifications and variations may be made therein without departing from the spirit and scope of the invention.

We claim:

1. A method of making a compound having the structural formula:

wherein at least one but no more than two of $R_1$, $R_2$, and $R_3$ are lipoate moiety of the formula:

and the other of said $R_1$, $R_2$, and $R_3$ are independently selected from $C_4$ to $C_{24}$ fatty acid moieties or OH, with the proviso that at least one of said $R_1$, $R_2$, and $R_3$ is a fatty acid moiety, comprising the steps of:

a. reacting in a reaction mixture lipoic acid or an ester thereof with a triglyceride in the presence of a lipase catalyst under conditions that permit transesterification of said lipoic acid or an ester thereof and said triglyceride; and b. recovering said compound from said reaction mixture.

2. The method of claim 1 wherein said fatty acid moieties are $C_6$ to $C_{23}$ fatty acid moieties.

3. The method of claim 2 wherein at least one of said fatty acid moieties are monoene $C_{16}$ or $C_{18}$ fatty acid moieties.

4. The method of claim 1 wherein said reaction mixture consists essentially of said lipoid acid.

5. The method of claim 1 wherein said reaction mixture comprises a solvent for said lipoic acid or ester thereof.

6. The method of claim 5 wherein said solvent comprises an alcohol.

7. The method of claim 1 wherein the source of said triglyceride is selected from the group consisting of vegetable oil, algal oil, marine oil and animal fat.

8. The method of claim 7 wherein the source of said triglyceride is selected from the group consisting of soybean oil, corn oil, sunflower seed oil, pennycress oil, high-oleic sunflower seed oil, canola oil, safflower oil, *cuphea* oil, jojoba oil, coconut oil, and palm kernel oil.

9. The method of claim 1 further comprising reacting said compound with a reducing agent effective to reduce said lipoate moiety to a dihydro-lipoate moiety of the formula 10. The method of claim 9 further comprising recovering a dihydrolipoyl derivative of said compound, wherein said dihydrolipoyl derivative is of the formula:

wherein at least one but no more than two of $R_1$, $R_2$, and $R_3$ are a dihydrolipoate moiety of the formula and the other of said $R_1$, $R_2$, and $R_3$ are independently selected from $C_4$ to $C_{24}$ fatty acid moieties or OH, with the proviso that at least one of said $R_1$, $R_2$, and $R_3$ is a fatty acid moiety.

* * * * *